United States Patent [19]

Forestier et al.

[11] Patent Number: 5,695,747
[45] Date of Patent: Dec. 9, 1997

[54] COSMETIC COMPOSITION CONTAINING A MIXTURE OF METAL OXIDE NANOPIGMENTS AND MELANINE PIGMENTS

[75] Inventors: Serge Forestier, Claye-Souilly; Isabelle Hansenne, Paris, both of France

[73] Assignee: L'Oreal, Paris, France

[21] Appl. No.: 451,982

[22] Filed: May 26, 1995

Related U.S. Application Data

[63] Continuation of Ser. No. 155,787, Nov. 23, 1993, abandoned, which is a continuation of Ser. No. 897,497, Jun. 12, 1992, abandoned.

[30] Foreign Application Priority Data

Jun. 14, 1991 [FR] France ................... 91 07324

[51] Int. Cl.$^6$ ................ A61K 7/42; A61K 7/40
[52] U.S. Cl. ............ 424/59; 424/63; 424/70.9; 514/972
[58] Field of Search ............. 424/59, 63, 401, 424/70.9; 514/972

[56] References Cited

U.S. PATENT DOCUMENTS

| 4,806,344 | 2/1989 | Gaskin | 424/59 |
| 4,806,360 | 2/1989 | Leong | 424/487 |
| 4,956,174 | 9/1990 | Lang | 424/59 |
| 4,961,754 | 10/1990 | Grollier | 8/423 |
| 5,028,417 | 7/1991 | Bhat | 424/59 |
| 5,032,390 | 7/1991 | Lwaya | 424/59 |
| 5,037,640 | 8/1991 | Schultz | 424/59 |
| 5,049,381 | 9/1991 | Schultz | 424/401 |
| 5,093,009 | 3/1992 | Haishi | 423/622 |
| 5,093,099 | 3/1992 | Haishi | 423/622 |
| 5,256,403 | 10/1993 | Gaskin | 424/59 |

FOREIGN PATENT DOCUMENTS

| 0379409 | 7/1990 | European Pat. Off. |
| 2207153 | 1/1989 | United Kingdom |

Primary Examiner—Sally Gardner-Lane
Attorney, Agent, or Firm—Nixon & Vanderhye, P.C.

[57] ABSTRACT

The invention relates to a cosmetic composition comprising, in a mixture, 0.10 to 15% by weight of metal oxide nanopigments chosen from titanium, zinc, cerium or zirconium oxide or mixtures thereof, with a mean diameter of less than 100 nm, and 0.001 to 2% by weight of melanin pigments derived from natural or synthetic sources with a mean diameter of between 10 and 20,000 nm, in a cosmetically acceptable carrier.

This composition is useful as a composition for protecting the human epidermis or the hair against UV rays or as make-up.

21 Claims, No Drawings

COSMETIC COMPOSITION CONTAINING A MIXTURE OF METAL OXIDE NANOPIGMENTS AND MELANINE PIGMENTS

This is a continuation of application Ser. No. 08/155,787, filed on Nov. 23, 1993, which was abandoned upon the filing hereof and which is a continuation of application Ser. No. 07/897,497, filed Jun. 12, 1992, now abandoned.

The subject of the present invention is a cosmetic composition containing metal oxide nanopigments mixed with melanin pigments, and its use for protecting the human epidermis and the hair and as make-up.

The use of conventional metal oxides of particle size between 100 and 700 nm, such as titanium oxide, in make-up as opacifying white pigment in combination with colored pigments, is known. Moreover, these compounds are particularly useful because of their diffusion and ultraviolet radiation reflecting properties which enable the human epidermis to be protected against ultraviolet rays. However, when the titanium oxide concentration in a cosmetic composition is increased in order to enhance the protection against ultraviolet rays, a cosmetic product is obtained which is difficult to apply to the skin, which is opaque and which causes whitening of the skin.

Attempts have therefore been made to reduce the size of the particles of metal oxide pigments. However, it was discovered that the exposure to light of metal oxide pigments with a particle size of less than 100 nm, known as "nanopigments", can generate a light-induced reaction which is prejudicial to the stability of the cosmetic compositions, in particular those containing lipids.

According to the invention, it has been discovered surprisingly that the addition of melanin pigments to a composition containing metal oxide nanopigments with a particle size of less than 100 nm makes it possible, on the one hand, to reduce or inhibit the light-induced reaction of metal oxide nanopigments and, on the other hand, to reduce the whitening of the skin conferred by these nanopigments.

The subject of the present invention is therefore a cosmetic composition comprising, in a mixture, at least one metal oxide nanopigment and at least one melanin pigment, in a cosmetically acceptable carrier.

In the present application, "nanopigment" will be understood to mean a pigment with a mean diameter of less than 100 nm, and preferably of between 5 and 50 nm.

The metal oxides are chosen from titanium, zinc, cerium or zirconium oxide or mixtures thereof.

The nanopigments may be coated or uncoated.

The coated pigments are pigments which have undergone one or more surface treatments of a chemical, electronic, mechanicochemical and/or mechanical nature with compounds such as those described for example in Cosmetics & Toiletries, February 1990, vol. 105, p.53–64, such as amino acids, beeswax, fatty acids, fatty alcohols, anionic surface-active agents, lecithins, sodium, potassium, zinc, iron or aluminum salts of fatty acids, (titanium or aluminum) metal alkoxides, polyethylene, silicones, proteins (collagen, elastin), alkanolamines, silicon oxides, metal oxides or sodium hexametaphosphate.

Coated pigments are more particularly titanium oxides coated with:

silica such as the product "SUNVEIL" from the company IKEDA, silica and iron oxide such as the product "SUNVEIL F" from the company IKEDA, silica and alumina such as the products "MICROTITANIUM DIOXIDE MT 500 SA" and "MICROTITANIUM DIOXIDE MT 100 SA" from the company TAYCA, "TIO-VEIL" from the company TIOXIDE, alumina such as the products "TIPAQUE TTO-55 (B)" and "TIPAQUE TTO-55 (A)" from the company ISHIHARA, and "UVT 14/4" from the company KEMIRA, alumina and aluminum stearate such as the product "MICROTITANIUM DIOXIDE MT 100 T" from the company TAYCA, alumina and aluminum laurate such as the product "MICROTITANIUM DIOXIDE MT 100 S" from the company TAYCA, iron oxide and iron stearate such as the product "MICROTITANIUM DIOXIDE MT 100 F" from the company TAYCA, zinc oxide and zinc stearate such as the product "BR 351" from the company TAYCA, silica, alumina and silicone such as the products "MICROTITANIUM DIOXIDE MT 600 SAS" and "MICROTITANIUM DIOXIDE MT 500 SAS" from the company TAYCA, silica, alumina, aluminum stearate and silicone such as the product "STT-30-DS" from the company TITAN KOGYO, alumina and silicone such as the product "TIPAQUE TTO-55 (S)" from the company ISHIHARA, triethanolamine such as the product "STT-65-S" from the company TITAN KOGYO, stearic acid such as the product "TIPAQUE TTO-55 (C)" from the company ISHIHARA, sodium hexametaphosphate such as the product "MICROTITANIUM DIOXIDE MT 150 W" from the company TAYCA.

Mixtures of metal oxides may also be mentioned, especially titanium dioxide and cerium dioxide, including the silica-coated equiponderous mixture of titanium dioxide and cerium dioxide sold by the company IKEDA under the name "SUNVEIL A", as well as the alumina-silica- and silicone-coated mixture of titanium oxide and zinc dioxide such as the product "M 261" sold by the company KEMIRA, or the alumina-, silica- and glycerin-coated mixture of titanium dioxide and zinc dioxide such as the product "M 211" sold by the company KEMIRA.

Uncoated titanium oxides are for example sold by the company TAYCA under the tradenames "MICROTITANIUM DIOXIDE MT 500 B" or "MICROTITANIUM DIOXIDE MT 600 B", by the company DEGUSSA under the name "P 25", by the company WACKHERR under the name "Oxyde de titane transparent PW", by the company MIYOSHI KASEI under the name "UFTR" and by the company TOMEN under the name "ITS".

Uncoated zinc oxides are for example sold by the company SUMITOMO under the name "ULTRA FINE ZINC OXIDE POWDER", by the company PRESPERSE under the name "FINEX 25" or by the company IKEDA under the name "MZO-25".

Uncoated cerium oxide is sold under the name "COLLOIDAL CERIUM OXIDE" by the company RHONE POULENC.

According to the invention, coated or uncoated titanium oxide nanopigments are particularly preferred.

The melanin pigments have a mean diameter of between 10 nm and 20,000 nm, preferably between 30 nm and 15,000 nm.

The melanin pigment(s) are derived from natural or synthetic sources and may be obtained (A) by oxidation of at least one indole compound, (B) by oxidative or enzymatic polymerization of melanin precursors, or (C) by extraction of melanin from substances containing it.

(A) The melanin pigments may firstly be obtained by oxidation of at least one indole compound chosen especially from those of the formula (I):

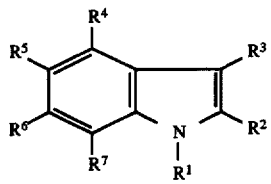

in which:

$R^1$ and $R^3$ represent independently of each other a hydrogen atom or a $C_1$–$C_4$ alkyl group;

$R^2$ represents a hydrogen atom, a $C_1$–$C_4$ alkyl group, a carboxyl group or a ($C_1$–$C_4$ alkoxy)carbonyl group;

$R^4$ and $R^7$ represent independently of each other a hydrogen atom, a hydroxyl group, a $C_1$–$C_4$ alkyl group, an amino group, a $C_1$–$C_4$ alkoxy group, a ($C_2$–$C_4$ acyl)oxy group or a ($C_2$–$C_4$ acyl)amino group;

$R^5$ represents a hydrogen atom, a hydroxyl group, a $C_1$–$C_4$ alkoxy group, a $C_1$–$C_4$ alkyl group, a halogen atom, an amino group, a ($C_2$–$C_{14}$ acyl)oxy group, a ($C_2$–$C_4$ acyl)amino group or a trimethylsilyloxy group;

$R^6$ represents a hydrogen atom, a hydroxyl group, a $C_1$–$C_4$ alkoxy group, an amino group, a ($C_2$–$C_4$ acyl)oxy group, a ($C_2$–$C_4$ acyl)amino group, a trimethylsilyloxy group or a ($C_2$–$C_4$ hydroxyalkyl)amino group;

it being possible for $R^5$ and $R^6$ also to form, together with the carbon atoms to which they are attached, a methylenedioxy ring which is optionally substituted by a $C_1$–$C_4$ alkyl or $C_1$–$C_4$ alkoxy group, or alternatively a carbonyldioxy ring;

at least one of the radicals $R^4$ to $R^7$ represents an OZ or $NHR^0$ group, at most one of the radicals $R^4$ to $R^7$ representing $NHR^0$ and at most two of the radicals $R^4$ to $R^7$ representing OZ and, in the case where Z represents a hydrogen atom, the two OH groups are in positions 5 and 6; and at least one of the radicals $R^4$ to $R^7$ represents a hydrogen atom, and in the case where only one of these radicals represents a hydrogen atom, only one radical among the radicals $R^4$ to $R^7$ then represents NHR or OZ, the other radicals representing a $C_1$–$C_4$ alkyl group;

the radical $R^0$ of the $NHR^0$ group denoting a hydrogen atom, a $C_2$–$C_4$ acyl or $C_2$–$C_4$ hydroxyalkyl group, and the radical Z of the OZ group denoting a hydrogen atom, a $C_2$–$C_{14}$ acyl group, a $C_1$–$C_4$ alkyl group or a trimethylsilyl group, and their alkali metal, alkaline-earth metal, ammonium or amine salts, as well as the hydrochlorides, hydrobromides, sulfates and methanesulfonates.

The indole compounds of formula (I) above are chosen preferably from 4-hydroxyindole, 5-hydroxyindole, 6-hydroxyindole, 7-hydroxyindole, 4-hydroxy-5-methoxyindole, 4-hydroxy-5-ethoxyindole, 2-carboxy-5-hydroxyindole, 5-hydroxy-6-methoxyindole, 6-hydroxy-7-methoxyindole, 5-methoxy-6-hydroxyindole, 5,6-dihydroxyindole, N-methyl-5,6-dihydroxyindole, 2-methyl-5,6-dihydroxyindole, 3-methyl-5,6-dihydroxyindole, 2,3-dimethyl-5,6-dihydroxyindole, 2-carboxy-5,6-dihydroxyindole, 4-hydroxy-5-methylindole, 2-carboxy-6-hydroxyindole, 6-hydroxy-N-methylindole, 2-ethoxycarbonyl-5,6-dihydroxyindole, 4-hydroxy-7-methoxy-2,3-dimethylindole, 4-hydroxy-5-ethoxy-N-methylindole, 6-hydroxy-5-methoxy-2-methylindole, 6-hydroxy-5-methoxy-2,3-dimethylindole, 6-hydroxy-2-ethoxycarbonylindole, 7-hydroxy-3-methylindole, 5-hydroxy-6-methoxy-2,3-dimethylindole, 5-hydroxy-3-methylindole, 5-acetoxy-6-hydroxyindole, 5-hydroxy-2-ethoxycarbonylindole, 6-hydroxy-2-carboxy-5-methylindole, 6-hydroxy-2-ethoxycarbonyl-5-methoxyindole, 6-N-β-hydroxyethylaminoindole, 4-aminoindole, 5-aminoindole, 6-aminoindole, 7-aminoindole, N-methyl-6-β-hydroxyethyl-aminoindole, 6-amino-2,3-dimethylindole, 6-amino-2,3,4,5-tetramethylindole, 6-amino-2,3,4-trimethylindole, 6-amino-2,3,5-trimethylindole, 6-amino-2,3,6-trimethylindole, 5,6-diacetoxyindole, 5-methoxy-6-acetoxyindole, 5,6-dimethoxyindole, 5,6-methylenedioxyindole, 5,6-trimethylsilyloxyindole, the phosphoric ester of 5,6-dihydroxyindole or from 5,6-dibenzyloxyindole, and from the addition salts of these compounds.

5,6-dihydroxyindole is particularly preferred.

The oxidation of the indole compound of formula (I) may be carried out in an aqueous or water-solvent(s) medium, in the open air, in the presence of or in the absence of an alkaline agent and/or an oxidation metal catalyst such as for example a cupric ion.

The reaction medium preferably consists of water and may, where appropriate, consist of a mixture of water and at least one solvent chosen such that it rapidly solubilizes the indole compound of formula (I). Among these solvents, there may be mentioned as examples $C_1$–$C_4$ lower alcohols such as ethyl alcohol, propyl or isopropyl alcohol, tert-butyl alcohol, alkylene glycols such as ethylene glycol, propylene glycol, alkaline glycol alkyl ethers such as ethylene glycol monomethyl, monoethyl and monobutyl ethers, propylene glycol or dipropylene glycol monomethyl ethers, and methyl lactate.

The oxidation may also be carried out using hydrogen peroxide in the presence of an alkaline agent such as, preferably, ammonium hydroxide, or in the presence of an iodide ion, the iodide being preferably an alkali metal, alkaline-earth metal or ammonium iodide.

The oxidation may also be carried out using periodic acid and its water-soluble salts and its derivatives, permanganates and bichromates such as sodium or potassium permanganates and bichromates, sodium hypochlorite, potassium ferricyanide, ammonium persulfate, silver oxide, lead oxide, ferric chloride, sodium nitrite, salts of rare earths including especially cerium, and organic oxidants chosen from ortho- and para-benzoquinones, ortho- and para-benzoquinone mono- or diimines, 1,2- and 1,4-naphthoquinones, or 1,2- and 1,4-naphthoquinone mono- or diimines as defined in application EP-A-0,376,776. The preferred periodic acid salt is sodium periodate.

It is possible to activate the oxidizing agents by a pH modifier.

An enzymatic oxidation may also be envisaged.

The insoluble product is isolated by filtration, centrifugation, freeze-drying or spray-drying; it is then ground or micronized in order to obtain the desired particle size.

(B) The melanin pigments according to the invention may also be obtained from oxidative or enzymatic polymerization of melanin precursors such as L-tyrosine, L-dopa, catechol and their derivatives.

(C) The melanin pigments according to the invention may be obtained from the extraction of the melanin of natural substances such as human hair, cephalopod ink (cuttlefish, octopuses), also known by the name sepiomelanin, in which case the pigment is ground and purified before being used.

(D) The melanin pigments according to the invention may finally be obtained by the culture of microorganisms. These microorganisms produce melanin either naturally, or by genetic modification or by mutagenesis. Modes of preparation of these melanines are described for example in Patent Application WO 9004029.

The melanin pigment(s) may be present at the surface or incorporated into an inorganic or organic inert particulate filler so as to constitute a synthetic composite melanin pigment formed in situ. In this case, the melanin pigment(s) may be derived from the oxidation of at least one indole compound of formula (I), as defined above, mixed with the filler, in an essentially non-solvent medium of the said filler, at a temperature which may range from room temperature up to about 100° C., or alternatively may be derived from the oxidative polymerization of melanin precursors on the filler.

The general conditions for oxidizing the indole compounds of formula (I) are the same as those mentioned above.

According to a first embodiment, the particulate filler is an inert inorganic filler advantageously consisting of particles with a particle size of less than 20,000 nm. Such inorganic filler-deposited composite melanin pigments as well as their preparation, are described in French Patent Application FR-A-2,618,069.

According to a second embodiment of the present invention, the particulate filler is an inert polymeric filler which is advantageously chosen from natural or synthetic, organic or inorganic polymers with a crystalline or amorphous cross-linked lattice, which have a molecular weight of between 5,000 and 5,000,000. Composite melanin pigments on a polymeric filler as well as their preparation, are described in European Patent Application No. 0379409.

The organic or synthetic polymers are in particular chosen from polymers derived from keratin, silk fibroin, chitin or cellulose, or from polyamides or homoor copolymers resulting from the polymerization of mono-or polyethylene, aliphatic or aromatic monomers containing a crosslinked, crystalline or amorphous lattice.

The keratin-derived polymers are chosen from animal or human keratins. Other keratin-derived polymers which may be used are chemically modified keratins having a molecular weight of between 10,000 and 250,000 and, in particular, partially hydrolized keratin (or keratin hydrolysate) having a molecular weight of between 50,000 and 200,000; this hydrolysate is preferably obtained by controlled alkaline hydrolysis; products of this type are for example sold under the name "KERASOL" by the company CRODA. Other modified keratins are sulfonic keratins with a molecular weight of between 10,000 and 100,000 which are obtained by oxidation of all or part of the disulfide bonds of the cystine groups of keratin to cystic acid groups.

The chitin-derived polymers comprise firstly chitin, which is a natural polymer, and the deacetylated derivative of chitin known under the name chitosan which is obtained by hydrolysis of the acetyl groups of chitin. Chitosan, as available commercially, is partially acetylated and contains 70 to 90% by weight of chitosan. It may also be used in the form of insoluble salts such as the sulfates and phosphates. Products of this type are sold for example under the name "KYTEX" by the company HERCULES.

The cellulosic polymers are chosen more particularly from microcrystalline celluloses such as the products sold under the name "AVICEL" by the company FMC CORPORATION.

Among the synthetic polymers, polyethylene, polypropylene, polystyrene, poly(methyl methacrylate) sold under the names "MICROPEARL M" and "MICROPEARL M100" by the company SERPIC, crosslinked poly(methyl methacrylate) such as the product sold under the name "MICROPEARL M 305" by the company SERPIC, may be more particularly mentioned. Other polymers are in particular chosen from linked poly-β-alanine as described in French Application 2,530,250, whose level of cross-linkage is between 1 and 15% and preferably between 1 and 8%.

Products known by the name of microsponges such as cross-linked polymers of styrene/divinylbenzene or of methyl methacrylate/ethylene glycol dimethacrylate or of vinyl stearate/divinylbenzene as described in patents WO-88/01164 and U.S. Pat. No. 4,690,825, may also be used as polymers. Such polymers essentially consist of cross-linked polymer beads comprising an inner pore lattice which is capable of retaining the melanin pigment. Other polymers of this type are hollow microspheres of a vinylidene chloride and acrylonitrile copolymer, which are sold under the name "EXPANCEL" by the company KEMA NORD; or alternatively porous microspheres of polyamide 12, polyamide 6 or copolyamide 6/12 which are sold under the name "ORGASOL" by the company ATOCHEM.

Silicone powders which are gums, resins and, more particularly, organopolysiloxane elastomers may also be used.

The metal oxide nanopigments are advantageously present in the cosmetic composition according to the invention at a concentration of between 0.1 and 15% by weight relative to the total weight of the composition, and preferably of between 0.5 and 10%.

The melanin pigments are advantageously present in the cosmetic composition according to the invention at a concentration of between 0.001 and 2%, preferably of between 0.0002 and 1% by weight relative to the total weight of the composition.

The melanin pigment/metal oxide nanopigment weight ratio is advantageously between 0.00007 and 10, preferably between 0.001 and 0.1.

The cosmetic composition of the invention may be used as a composition for protecting the human epidermis or the hair against ultraviolet rays, as anti-sun composition or as make-up.

This composition may be provided in particular in the form of a lotion, thickened lotion, gel, cream, milk, powder, solid stick and may be optionally packaged as an aerosol and provided in the form of a foam or spray.

It may contain the cosmetic adjuvants normally used, such as fatty substances, organic solvents, silicones, thickeners, demulcents, UV-A, UV-B or broad band sunscreen agents, antifoaming agents, moisturizing agents, perfumes, preservatives, surface-active agents, fillers, sequestrants, anionic, cationic, nonionic or amphoteric polymers or mixtures thereof, propellants, alkalizing or acidifying agents, colorants, pigments with a particle size greater than 100 nm, such as iron oxides or any other ingredient normally used in cosmetics.

Among the organic solvents, lower alcohols and polyols such as ethanol, isopropanol, propylene glycol, glycerin and sorbitol may be mentioned.

The fatty substances may consist of an oil or a wax or a mixture thereof, of fatty acids, fatty acid esters, fatty alcohols, vaseline, paraffin, lanolin, hydrogenated lanolin or acetylated lanolin.

The oils are chosen from animal, vegetable, mineral or synthetic oils, and in particular from hydrogenated palm oil, hydrogenated castor oil, vaseline oil, paraffin oil, Purcellin oil, silicone oils and isoparaffins.

The waxes are chosen from animal, fossil, vegetable, mineral or synthetic waxes. Beeswaxes, Carnauba, Candelilla, sugar cane or japan waxes, ozokerites, Montan wax, microcrystalline waxes, paraffins or silicone waxes and resins may particularly be mentioned.

The fatty acid esters are for example isopropyl myristate, isopropyl adipate, isopropyl palmitate, octyl palmitate, $C_{12}$–$C_{15}$ fatty alcohol benzoates ("FINSOLV TN" from FINETEX), oxypropylenated myristic alcohol containing 3 moles of propylene oxide ("WITCONOL APM" from WITCO), capric and caprylic acid triglycerides ("MIGLYOL 812" from HULS).

The cosmetic composition according to the invention may contain thickeners which may be chosen from cross-linked or non cross-linked acrylic acid polymers, and particularly polyacrylic acids which are cross-linked using a polyfunctional agent, such as the products sold under the name "CARBOPOL" by the company GOODRICH, cellulose derivatives such as methylcellulose, hydroxyethyl cellulose, hydroxypropyl methylcellulose, sodium salts of carboxymethylcellulose, and mixtures of cetylstearyl alcohol and oxyethylenated cetylstearyl alcohol containing 33 moles of ethylene oxide.

The products resulting from the ionic interaction of a cationic polymer, consisting of a copolymer of cellulose or a cellulose derivative grafted via a water-soluble quaternary ammonium monomer salt, and an anionic carboxylic polymer such as those described in French Patent FR-2,598,611, may also be used. The product from the ionic interaction of a hydroxyethyl cellulose copolymer grafted via a radical-based method, via diallyldimethylammonium chloride, such as the polymer marketed under the name "CELQUAT L 200" by the company National Starch, with either ethylene and maleic anhydride copolymers such as the products sold under the name "EMA 31" by the company MONSANTO, or 50/50 methacrylic acid and methyl methacrylate copolymers, are preferably used.

Another product of this type which may be used is the product resulting from the ionic interaction of the hydroxyethyl cellulose copolymer grafted via a radical-based method, via diallyldimethylammonium chloride, with a cross-linked anionic carboxylic polymer such as the cross-linked methacrylic acid and ethyl acrylate copolymers sold under the name "VISCOATEX" 538,46 or 50 by the company COATEX.

When the cosmetic composition according to the invention is used for protecting the human epidermis against UV rays or as anti-sun composition, it may be provided in the form of a suspension or dispersion in solvents or fatty substances, or alternatively in the form of an emulsion such as a cream or a milk, in the form of an ointment, gel, solid stick or aerosol foam. The emulsions may contain, in addition, anionic, nonionic, cationic or amphoteric surface-active agents.

When the cosmetic composition according to the invention is used for protecting the hair, it may be provided in the form of a rinse-off shampoo, lotion, gel or composition to be applied before or after shampooing, before or after dyeing or bleaching, before, during or after permanent waving or hair straightening, a hair styling or treatment lotion or gel, a lotion or gel for blow drying or hair setting, hair lacquer, or composition for permanent waving or hair straightening, for dyeing or bleaching the hair.

When the composition is used as make-up for the eyelashes, the eyebrows, the skin or the hair, such as cream for treating the epidermis, foundation, lipstick, eyeshadow, blusher, eyeliner, mascara, or coloring gel, it may be provided in anhydrous or aqueous solid or pasty form, as oil-in-water or water-in-oil emulsions, as suspensions or alternatively as gels.

The subject of the invention is also a process for protecting the human epidermis and the hair against ultraviolet radiation as well as a process for applying make-up which consists in applying to the skin or the hair an effective amount of the above cosmetic composition.

The subject of the invention is also the use of melanin pigments derived from natural or synthetic sources, with a mean diameter of between 10 nm and 20,000 nm, for reducing or inhibiting the light-induced reaction of metal oxide nanopigments exposed to light, these metal oxides being chosen from titanium, zinc, cerium, or zirconium oxides or mixtures thereof, with a mean diameter of 100 nm, and preferably of between 5 and 50 nm.

The invention will be better illustrated by the non-limitative examples below.

EXAMPLE 1

An oil-in-water anti-sun emulsion of the following composition is prepared:

| | |
|---|---|
| melanin pigment obtained by oxidation of 5,6-dihydroxyindole | 0.1 g |
| alumina- and aluminum stearate- coated titanium oxide sold under the name "MICROTITANIUM DIOXIDE MT 100T" by the company TAYCA | 6.5 g |
| mixture of cetylstearyl alcohol and oxyethylenated cetylstearyl alcohol containing 33 moles of ethylene oxide sold under the name "SINNOWAX AO" by the company HENKEL | 7.0 g |
| non-self-emulsifying glycerol mono- and distearate mixture | 2.0 g |
| vaseline oil | 15.0 g |
| cetyl alcohol | 1.5 g |
| polydimethylsiloxane | 1.5 g |
| glycerin | 20.0 g |
| preservatives, perfume qs | |
| water qs | 100 g |

EXAMPLE 2

An oil-in-water anti-sun emulsion of the following composition is prepared:

| | |
|---|---|
| melanin pigment obtained by oxidation of 5,6-dihydroxyindole | 0.015 g |
| alumina- and aluminum stearate- coated titanium oxide sold under the name "MICROTITANIUM DIOXIDE MT 100T" by the company TAYCA | 6.5 g |
| mixture of cetylstearyl alcohol and oxyethylenated cetylstearyl alcohol containing 33 moles of ethylene oxide sold under the name "SINNOWAX AO" by the company HENKEL | 7.0 g |
| non-self-emulsifying glycerol mono- and distearate mixture | 2.0 g |
| vaseline oil | 15.0 g |
| cetyl alcohol | 1.5 g |
| polydimethylsiloxane | 1.5 g |
| glycerin | 20.0 g |
| preservatives, perfume qs | |
| water qs | 100 g |

EXAMPLE 3

An oil-in-water anti-sun emulsion of the following composition is prepared:

| | |
|---|---|
| melanin pigment obtained by oxidation of 5,6-dihydroxyindole | 0.1 g |
| alumina- and aluminum stearate- coated titanium oxide sold under the name "MICROTITANIUM DIOXIDE MT 100T" by the company TAYCA | 6.5 g |
| mixture of cetylstearyl alcohol and oxyethylenated cetylstearyl alcohol containing 33 moles of ethylene oxide sold under the name "SINNOWAX AO" by the company HENKEL | 7.0 g |
| non-self-emulsifying glycerol mono- and distearate mixture | 2.0 g |
| vaseline oil | 15.0 g |
| cetyl alcohol | 1.5 g |
| polydimethylsiloxane | 1.5 g |
| glycerin | 20.0 g |
| yellow iron oxide | 0.4 g |
| red iron oxide | 0.2 g |
| preservatives, perfume qs | |
| water qs | 100 g |

EXAMPLE 4

A water-in-oil anti-sun emulsion of the following composition is prepared:

| | |
|---|---|
| melanin pigment obtained by oxidation of 5,6-dihydroxyindole | 0.3 g |
| zinc oxide sold under the name "ULTRA FINE ZINC OXIDE POWDER" by the company SUMITOMO | 3.0 g |
| vaseline oil | 15.0 g |
| oxyethylenated glycerol and sorbitan hydroxystearate containing 2.5 moles of ethylene oxide and oxypropylenated glycerol and sorbitan hydroxystearate containing 1.5 moles of propylene oxide sold under the name "ARLACEL 78.0" by the company ICI | 5.0 g |
| magnesium sulfate | 0.7 g |
| preservative qs | |
| water qs | 100 g |

EXAMPLE 5

A water-in-oil anti-sun emulsion of the following composition is prepared:

| | |
|---|---|
| melanin pigment obtained by oxidation of 5,6-dihydroxyindole | 0.002 g |
| alumina- and aluminum stearate-coated titanium oxide sold under the name "MICROTITANIUM DIOXIDE MT 100T" by the company TAYCA | 6.5 g |
| vaseline oil | 15.0 g |
| oxyethylenated glycerol and sorbitan hydroxystearate containing 2.5 moles of ethylene oxide and oxypropylenated glycerol and sorbitan hydroxystearate containing 1.5 moles of propylene oxide sold under the name "ARLACEL 780" by the company ICI | 5.0 g |
| magnesium sulfate | 0.7 g |
| preservative qs | |
| water qs | 100 g |

EXAMPLE 6

A colored cream of the following composition is prepared:

| | |
|---|---|
| non-self-emulsifying glycerol mono- and distearate mixture | 3.5 g |
| glycerol isostearate | 1.8 g |
| mixture of mineral oil and lanolin alcohol sold under the name "AMERCHOL L-101" by the company AMERCHOL | 3.1 g |
| isopropyl palmitate | 7.6 g |
| octyl palmitate | 7.0 g |
| ultramarine violet | 0.75 g |
| titanium dioxide with a particle size of 200–300 nm | 3.0 g |
| yellow iron oxide | 1.0 g |
| red iron oxide | 0.6 g |
| black iron oxide | 0.08 g |
| preservatives | 0.5 g |
| perfume | 0.3 g |
| aluminum and magnesium silicate | 1.5 g |
| talc | 4.46 g |
| triethanolamine | 1.2 g |
| cellulose gum | 0.05 g |
| xanthan gum | 0.15 g |
| cyclomethicone (CTFA Dictionary name; cyclic dimethyl polysiloxane) | 7.5 g |
| propylene glycol | 3.0 g |
| glycerin | 2.0 g |
| stearic acid | 2.5 g |
| titanium dioxide with a particle size of 30–40 nm | 6.0 g |
| melanin pigment obtained by oxidation of 5,6-dihydroxyindole | 0.02 g |
| water qs | 100 g |

The fatty phase containing the oils and stearic acid and the aqueous phase containing triethanolamine are separately heated to 80° C.

The mixture is emulsified at 80° C. and cooled slowly. During the cooling, the mixture of pigments, previously ground in propylene glycol and cyclomethicone are added.

EXAMPLE 7

A foundation of the following composition is prepared:

| | |
|---|---|
| triethanolamine | 1.0 g |
| polyethylene glycol stearate containing 2 moles of ethylene oxide | 0.53 g |
| non-self-emulsifying glycerol mono- and distearate mixture | 0.35 g |
| aluminum and magnesium silicate | 1.5 g |
| yellow iron oxide | 0.9 g |
| red iron oxide | 0.5 g |
| black iron oxide | 0.2 g |
| titanium dioxide with a particle size of 200–300 nm | 5.4 g |
| titanium dioxide with a particle size of 30–40 nm | 8.0 g |
| melanin pigment obtained by oxidation of 5,6-dihydroxyindole | 0.02 g |
| preservatives | 0.5 g |
| mixture of polyethylene glycol containing 6 moles of ethylene oxide and polyethylene glycol containing 32 moles of ethylene oxide sold under the name "CARBOWAX 1450" by the company UNION CARBIDE | 9.0 g |
| cellulose gum | 0.02 g |
| polyethylene | 9.3 g |
| cyclomethicone (CTFA Dictionary name; cyclic dimethylpolysiloxane) | 14.0 g |
| propylene glycol | 6.0 g |
| glycerin | 3.0 g |
| stearic acid | 2.2 g |
| water qs | 100 g |

The composition is prepared in a manner similar to Example 6.

EXAMPLE 8

Black mascara

| | |
|---|---|
| triethanolamine stearate | 15.0 g |
| beeswax | 5.0 g |
| paraffin | 3.0 g |
| carnauba wax | 10.0 g |
| propyl para-hydroxybenzoate | 0.2 g |
| methyl para-hydroxybenzoate | 0.2 g |
| arabic gum | 3.0 g |
| hydroxyethyl cellulose | 0.3 g |
| melanin pigment obtained by oxidation of 5,6-dihydroxyindole | 1.0 g |
| titanium dioxide with a mean particle size of 30–40 nm | 2.0 g |
| water qs | 100 g |

EXAMPLE 9

An oil-in-water anti-sun emulsion of the following composition is prepared:

| | |
|---|---|
| cerium oxide (mean diameter 12 nanometers) in aqueous suspension containing 20% AI, sold under the name "COLLOIDAL CERIUM OXIDE" by the company RHONE POULENC | 3.0 g AI |
| melanin pigment obtained by oxidation of 2-methyl-5,6-dihydroxyindole | 0.05 g |
| mixture of cetylstearyl alcohol and oxyethylenated cetylstearyl alcohol containing 33 moles of ethylene oxide sold under the name "SINNOWAX AO" by the company HENKEL | 7.0 g |
| glycerol stearate sold under the name "GELEOL" by the company GATTEFOSSE | 2.0 g |
| cetyl alcohol | 1.5 g |
| vaseline oil | 15.0 g |
| glycerin qs | 3.0 g |
| water qs | 100 g |

EXAMPLE 10

A hair styling gel, for protecting against UV radiation and for dyeing, of the following composition is prepared:

| | |
|---|---|
| titanium dioxide (diameter: 15 to 40 nanometers) sold under the name "P 25" by the company DEGUSSA | 0.2 g |
| cross-linked methacrylic acid and ethylacrylate copolymer sold at 30% AI under the name "VISCOATEX 46" by the company COATEX | 1.35 g AI |
| hydroxyethyl cellulose and diallyldimethyl-ammonium chloride copolymer sold under the name "CELQUAT L 200" by the company NATIONAL STARCH | 1.0 g |
| melanin pigment obtained by oxidation of 5,6-dihydroxyindole | 1.0 g |
| siliconized cationic polymer sold at a concentration of 35% AI under the name "Emulsion cationique DC929" by the company DOW CORNING | 0.3 g |
| 2-amino-2-methyl-1-propanol qs pH 7.5 perfume, preservative qs | |
| water qs | 100 |

EXAMPLE 11

An oil-in-water anti-sun emulsion of the following composition is prepared:

| | |
|---|---|
| alumina- and aluminum stearate- coated titanium oxide sold under the name "MICROTITANIUM DIOXIDE MT 100T" by the company TAYCA | 5.0 g |
| melanin pigment obtained by oxidation of 2-methyl-5,6-dihydroxyindole hydrobromide | 0.1 g |
| mixture of cetylstearyl alcohol and oxyethylenated cetylstearyl alcohol containing 33 moles of ethylene oxide sold under the name "SINNOWAX AO" by the company HENKEL | 7.0 g |
| glycerol stearate sold under the name "GELEOL" by the company GATTEFOSSE | 2.0 g |
| cetyl alcohol | 1.5 g |
| vaseline oil | 15.0 g |
| glycerin | 3.0 g |
| preservative, perfume qs | |
| water qs | 100 g |

EXAMPLE 12

An oil-in-water anti-sun emulsion of the following composition is prepared:

| | |
|---|---|
| alumina- and aluminum stearate- coated titanium oxide sold under the name "MICROTITANIUM DIOXIDE MT 100T" by the company TAYCA | 5.0 g |
| melanin pigment obtained by oxidation of 2-methyl-5,6-dihydroxyindole | 0.1 g |
| mixture of cetylstearyl alcohol and oxyethylenated cetylstearyl alcohol containing 33 moles of ethylene oxide sold under the name "SINNOWAX AO" by the company HENKEL | 7.0 g |
| glycerol stearate sold under the name "GELEOL" by the company GATTEFOSSE | 2.0 g |
| cetyl alcohol | 1.5 g |
| vaseline oil | 15.0 g |
| glycerin | 3.0 g |
| preservative, perfume qs | |
| water qs | 100 g |

EXAMPLE 13

Hair styling gel

| | |
|---|---|
| polyvinylpyrrolidone and vinyl acetate copolymer (65/35 by weight) sold by the company GAF under the name PVP/VA S 630 | 0.5 g |
| cross-linked polyacrylic acid sold under the name "CARBOPOL 940" (MW 4,000,000) by the company GOODRICH | 0.5 g |
| titanium dioxide sold by the company DEGUSSA under the name "P 25" | 0.2 g |
| melanin pigment obtained by oxidation of 5,6-dihydroxyindole | 2.0 g |
| ethyl alcohol | 17.2 g |
| perfume, colorant, preservative qs triethanolamine qs pH : 7.5 | |
| water qs | 100 g |

We claim:

1. A cosmetic composition for application to the hair or skin comprising in a cosmetically acceptable carrier, a mixture of at least one metal oxide nanopigment selected from the group consisting of titanium oxide, zinc oxide, cerium oxide, zirconium oxide and mixtures thereof, said metal oxide nanopigment having a mean diameter in the range of 5 to 50 nm, and being present in said composition in an amount ranging from 0.1 to 15 percent by weight relative to the total weight of said composition, and at least one melanin pigment having a mean diameter ranging from 10 nm to 20,000 nm and being present in an amount ranging from 0.001 to 2 percent by weight relative to the total weight of said composition so as to effectively reduce or inhibit light-induced reaction of said metal oxide nanopigment or reduce whitening of the skin imparted by said metal oxide nanopigment, or both, and wherein the melanin pigment/metal oxide nanopigment weight ratio ranges from 0.00007 to 10.

2. The cosmetic composition of claim 1, wherein said metal oxide nanopigment is titanium oxide.

3. The cosmetic composition of claim 1, wherein said melanin pigment has a mean diameter ranging from 30 to 15,000 nm.

4. The cosmetic composition of claim 1, wherein said metal oxide nanopigment is an uncoated pigment.

5. The cosmetic composition of claim 1, wherein said metal oxide nanopigment is a coated pigment having undergone at least one surface treatment, of a chemical, electronic, mechanicochemical or mechanical nature, with a compound selected from the group consisting of an amino acid; beeswax; a fatty acid; a fatty alcohol; an anionic surface-active agent; a lecithin; a sodium, potassium, zinc, iron or aluminum salt of a fatty acid; sodium hexametaphosphate; a metal alkoxide; polyethylene; a silicone; a protein; an alkanolamine; a silicon oxide; and a metal oxide.

6. The cosmetic composition of claim 5, wherein said metal oxide nanopigment is titanium oxide pigment coated with (i) silica, (ii) silica and iron oxide, (iii) silica and alumina, (iv) alumina, (v) alumina and aluminum stearate, (vi) alumina and aluminum laureate, (vii) iron oxide and iron stearate, (viii) zinc oxide and zinc stearate, (ix) silica, alumina and a silicone, (x) silica, alumina, aluminum stearate and a silicone, (xi) alumina and a silicone, (xii) triethanolamine, (xiii) stearic acid or (xiv) sodium hexametaphosphate.

7. The cosmetic composition of claim 5, wherein said coated metal oxide nanopigment is selected from the group consisting of a silica coated mixture of titanium dioxide and cerium dioxide, an alumina-, silica- and silicone-coated mixture of titanium dioxide and zinc dioxide and an alumina-, silica- and glycerin-coated mixture of titanium dioxide and zinc dioxide.

8. The cosmetic composition of claim 1, wherein said melanin pigment is selected from the group consisting of a product obtained by oxidation of at least one indole compound, by oxidation or enzymatic polymerization of a melanin precursor or by extraction of melanin from a substance containing melanin.

9. The cosmetic composition of claim 8, wherein said melanin pigment is obtained by oxidation of at least one indole compound of formula

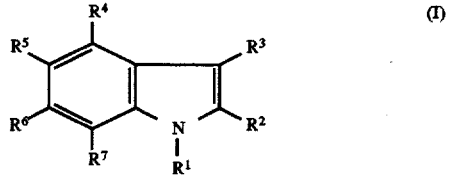

(I)

wherein $R^1$ and $R^3$, each independently, represent hydrogen, or a $C_1$–$C_4$ alkyl;

$R^2$ represents hydrogen, $C_1$–$C_4$ alkyl, carboxyl, or ($C_1$–$C_4$ alkoxy) carbonyl;

$R^4$ and $R^7$, each independently, represent hydrogen, hydroxyl, $C_1$–$C_4$ alkyl, amino, $C_1$–$C_4$ alkoxy, ($C_2$–$C_4$ acyl) oxy or ($C_2$–$C_4$ acyl) amino;

$R^5$ represents hydrogen, hydroxyl, $C_1$–$C_4$ alkoxy, $C_1$–$C_4$ alkyl, halogen, amino, ($C_2$–$C_4$ acyl) oxy, ($C_2$–$C_4$ acyl) amino or trimethylsilyloxy;

$R^6$ represents hydrogen, hydroxyl, $C_1$–$C_4$ alkoxy, amino, ($C_2$–$C_4$ acyl) oxy, ($C_2$–$C_4$ acyl) amino, trimethylsilyloxy or ($C_2$–$C_4$ hydroxyalkyl) amino;

it being possible for $R^5$ and $R^6$ also to form, together with the carbon atoms to which they are attached, a methylenedioxy ring which is optionally substituted by a $C_1$–$C_4$ alkyl or $C_1$–$C_4$ alkoxy group, or alternatively a carbonyldioxy ring;

at least one of said $R^4$ to $R^7$ radicals represents an OZ or NHR° group, at most one of said radicals $R^4$ to $R^7$ representing NHR° and at most two of said radicals $R^4$ to $R^7$ representing OZ and, in the case where Z represents hydrogen, the two OH groups are in positions 5 and 6;

and at least one of said $R^4$ to $R^7$ radicals represents hydrogen, and in the case where only one of said $R^4$ to $R^7$ radicals represents hydrogen, only one radical among said $R^4$ to $R^7$ radicals represents NHR° or OZ, the other radicals representing $C_1$–$C_4$ alkyl;

said radical R° of said NHR° group representing hydrogen, $C_2$–$C_4$ acyl or $C_2$–$C_4$ hydroxyalkyl, and said radical Z of said OZ group representing hydrogen, $C_2$–$C_{14}$ acyl, $C_1$–$C_4$ alkyl or trimethylsilyl, the alkali metal, alkaline-earth metal, ammonium or amine salts thereof and the hydrochloride, hydrobromide, sulfate or methanesulfonate of said indole compound.

10. The cosmetic composition as claimed in claim 9, wherein said indole compound is selected from the group consisting of 4-hydroxyindole,
5-hydroxyindole,
6-hydroxyindole,
7-hydroxyindole,
4-hydroxy-5-methoxyindole,
4-hydroxy-5-ethoxyindole,
2-carboxy-5-hydroxyindole,
5-hydroxy-6-methoxyindole,
6-hydroxy-7-methoxyindole,
5-methoxy-6-hydroxyindole,
5,6-dihydroxyindole,
N-methyl-5,6-dihydroxyindole,
2-methyl-5,6-dihydroxyindole,
3-methyl-5,6-dihydroxyindole,
2,3-dimethyl-5,6-dihydroxyindole,
2-carboxy-5,6-dihydroxyindole,
4-hydroxy-5-methylindole,
2-carboxy-6-hydroxyindole,
6-hydroxy-N-methylindole,
2-ethoxycarbonyl-5,6-dihydroxyindole,
4-hydroxy-7-methoxy-2,3-dimethylindole,
4-hydroxy-5-ethoxy-N-methylindole,
6-hydroxy-5-methoxy-2-methylindole,
6-hydroxy-5-methoxy-2,3-dimethylindole,
6-hydroxy-2-ethoxycarbonylindole,
7-hydroxy-3-methylindole,
5-hydroxy-6-methoxy-2,3-dimethylindole,
5-hydroxy-3-methylindole,
5-acetoxy-6-hydroxyindole,
5-hydroxy-2-ethoxycarbonylindole,
6-hydroxy-2-carboxy-5-methylindole, 6-hydroxy-2-ethoxycarbonyl-5-methoxyindole, 6-N-β-hydroxyethylaminoindole, 4-aminoindole, 5-aminoindole, 6-aminoindole, 7-aminoindole, N-methyl-6-β-hydroxyethylaminoindole, 6-amino-2,3-dimethylindole, 6-amino-2,3,4,5-tetramethylindole, 6-amino-2,3,4-trimethylindole, 6-amino-2,3,5-trimethylindole, 6-amino-2,3,6-trimethylindole, 5,6-diacetoxyindole, 5-methoxy-6-acetoxyindole, 5,6-dimethoxyindole, 5,6-methylenedioxyindole, 5,6-trimethylsilyloxyindole, the phosphoric ester of 5,6-dihydroxyindole, 5,6-dibenzyloxyindole, and the addition salts of these compounds.

11. The cosmetic composition of claim 10, wherein said indole compound is 5,6-dihydroxyindole.

12. The cosmetic composition of claim 1, wherein said melanin pigment is a synthetic composite melanin pigment deposited at the surface or incorporated into an inorganic or organic inert particulate filler.

13. The cosmetic composition of claim 12, wherein said particulate filler comprises an inert inorganic particle having a particle size of less than 20,000 nm, or a natural or synthetic, organic or inorganic polymer having a crystalline or amorphous crosslinked lattice and having a molecular weight ranging from 5,000 to 5,000,000.

14. The cosmetic composition of claim 1 in a form wherein the cosmetically acceptable carrier is selected from the group consisting of a lotion, a gel, a cream, a milk, a powder, a solid stick, a foam and a spray.

15. The cosmetic composition of claim 14, which also contains a cosmetic adjuvant selected from the group consisting of a fatty substance; an organic solvent; a silicone; a thickener; a demulcent; a UV-A, UV-B or broad band sunscreen agent; an antifoaming agent; a moisturizing agent; a perfume; a preservative; a surface-active agent; a filler; a sequesterant; an anionic, cationic, nonionic or amphoteric polymer or mixture thereof; a propellant; an alkalizing or acidifying agent; a colorant; and a pigment having a particle size greater than 100 nm.

16. The cosmetic composition of claim 1 comprising a composition for protecting human epidermis against ultraviolet rays or an anti-sun composition, said composition being in the form of a suspension or dispersion in a solvent or a fatty substance, or in the form of an emulsion, or in the form of an ointment, a gel, a solid stick or an aerosol foam.

17. The cosmetic composition of claim 1, for use in protecting hair against ultraviolet rays, said composition being in a form of a rinse-off shampoo; a lotion; a gel; or in the form of a composition to be applied (a) before or after shampooing, (b) before or after dyeing or bleaching, (c) before, during or after permanent waving or hair straightening; a hair styling or treatment lotion or gel; a lotion or gel for blow drying or hair setting; a hair lacquer; a composition for permanent waving or hair straightening; or a composition for dyeing or bleaching hair.

18. The cosmetic composition of claim 1, comprising a make-up for eyelashes, eyebrows, skin or hair, said make-up being selected from the group consisting of a cream for treating the epidermis; a foundation; a lipstick; an eyeshadow; a blusher; an eyeliner; a mascara; or a coloring gel and wherein said cosmetically acceptable carrier is selected from the group consisting of an anhydrous solid, an aqueous solid and a paste.

19. A process for protecting human skin and hair against ultraviolet radiation which comprises applying to said skin or hair an ultraviolet protection amount of said cosmetic composition as claimed in claim 1.

20. A method for reducing or inhibiting light-induced reaction of a metal oxide nanopigment exposed to light, said metal oxide nanopigment being selected from the group consisting of titanium oxide, zinc oxide, cerium oxide, zirconium oxide and a mixture thereof and having a mean diameter in the range of 5 to 50 nm, said method comprising combining said nanopigment with a melanin pigment derived from a natural or synthetic source and having a mean diameter ranging from 10 nm to 20,000 nm.

21. The composition according to claim 1, wherein said metal oxide nanopigment is zinc oxide.

* * * * *